United States Patent
Qian et al.

(10) Patent No.: US 9,522,099 B2
(45) Date of Patent: *Dec. 20, 2016

(54) DENTAL COMPOSITIONS HAVING SPECIAL FUNCTIONALITY AND A TRI-BARREL PACKAGING AND DELIVERY SYSTEM THEREFOR

(75) Inventors: Xuejun Qian, Foothill Ranch, CA (US); David Tobia, Ladera Ranch, CA (US)

(73) Assignee: Kerr Corporation, Orange, CA (US)

( * ) Notice: Subject to any disclaimer, the term of this patent is extended or adjusted under 35 U.S.C. 154(b) by 911 days.

This patent is subject to a terminal disclaimer.

(21) Appl. No.: 13/288,347

(22) Filed: Nov. 3, 2011

(65) Prior Publication Data
US 2012/0115106 A1    May 10, 2012

Related U.S. Application Data

(60) Provisional application No. 61/410,171, filed on Nov. 4, 2010, provisional application No. 61/410,443, filed on Nov. 5, 2010, provisional application No. 61/410,565, filed on Nov. 5, 2010.

(51) Int. Cl.
*A61K 6/083* (2006.01)
*A61K 6/00* (2006.01)

(52) U.S. Cl.
CPC .............. *A61K 6/0023* (2013.01); *A61K 6/083* (2013.01); *A61K 6/005* (2013.01)

(58) Field of Classification Search
CPC .................................. A61K 6/005; A61K 6/083
USPC ........................................................ 523/116
See application file for complete search history.

(56) References Cited

U.S. PATENT DOCUMENTS

| | | | |
|---|---|---|---|
| 4,467,079 A * | 8/1984 | Hechenberger et al. ....... | 526/90 |
| 4,567,030 A | 1/1986 | Yuasa et al. | |
| 4,678,436 A | 7/1987 | Kondo et al. | |
| 4,772,325 A | 9/1988 | Kwan et al. | |
| 4,775,585 A | 10/1988 | Hagiwara et al. | |
| 4,792,632 A | 12/1988 | Ellrich et al. | |
| 4,911,899 A | 3/1990 | Hagiwara et al. | |
| 5,154,762 A * | 10/1992 | Mitra et al. ..................... | 106/35 |
| 5,451,343 A | 9/1995 | Neckers et al. | |
| 5,609,675 A | 3/1997 | Noritake et al. | |
| 5,623,080 A | 4/1997 | Neckers et al. | |
| 5,824,720 A | 10/1998 | Nowak et al. | |
| 6,214,101 B1 | 4/2001 | Nakaseko | |
| 6,703,518 B1 | 3/2004 | Xu et al. | |
| 6,872,244 B2 | 3/2005 | Kobayashi et al. | |
| 6,924,325 B2 | 8/2005 | Qian | |
| 7,166,651 B2 | 1/2007 | Qian | |
| 7,214,726 B2 | 5/2007 | Qian | |
| 7,906,564 B2 | 3/2011 | Jia et al. | |
| 2003/0083398 A1* | 5/2003 | Kawashima et al. ......... | 523/115 |
| 2005/0014861 A1 | 1/2005 | Qian | |
| 2005/0154081 A1 | 7/2005 | Yin et al. | |
| 2006/0004122 A1 | 1/2006 | Hecht et al. | |
| 2007/0197682 A1* | 8/2007 | Jia et al. ....................... | 523/116 |
| 2007/0203257 A1 | 8/2007 | Qian | |
| 2007/0264615 A1 | 11/2007 | Ruppert et al. | |
| 2009/0012209 A1 | 1/2009 | Eckhardt et al. | |
| 2009/0048364 A1 | 2/2009 | Liu | |
| 2010/0010115 A1 | 1/2010 | Kohro et al. | |
| 2010/0240795 A1 | 9/2010 | Burtscher et al. | |

FOREIGN PATENT DOCUMENTS

| | | |
|---|---|---|
| DE | 102004031524 A1 | 1/2006 |
| DE | 102007054888 A1 | 5/2009 |
| EP | 079703 A1 | 5/1983 |
| EP | 0115410 A2 | 8/1984 |
| EP | 0541493 A1 | 5/1993 |
| EP | 1408060 A1 | 4/2004 |
| JP | 2004-051555 A | 2/2004 |
| WO | 0230363 A2 | 4/2002 |
| WO | 2007041266 A1 | 4/2007 |

OTHER PUBLICATIONS

Anonymous, Color Indicated Dental Compositions for Use as a Bonding Agent, Self-Etch Primer, and Surface Sealant, Research Disclosure, vol. 470, No. 44, Mason Publications, Hampshire, GB, Jun. 1, 2003, 2 pp.
European Patent Office, Search Report and Preliminary Opinion issued in related EP Application No. 11187937.5, dated Sep. 30, 2013, 7 pp.
European Patent Office, Search Report and Preliminary Opinion issued in related EP Application No. 11187940.9, dated Oct. 2, 2013, 6 pp.
European Patent Office, Search Report and Preliminary Opinion issued in corresponding EP Application No. 11187943.3, dated Oct. 11, 2013, 8 pp.
Database WPI Week 200418, Thomson Scientific, London, GB, XP002713349, 2 pp.
State Intellectual Property Office of the P.R.C., Chinese First Office Action and English translation, dated Jun. 25, 2014, 12 pp.
U.S. Patent and Trademark Office, Final Office Action issued in related U.S. Appl. No. 13/288,420 dated Feb. 4, 2015, 15 pp.

* cited by examiner

*Primary Examiner* — Michael Pepitone
(74) *Attorney, Agent, or Firm* — Wood Herron & Evans LLP

(57) ABSTRACT

A self-cure, dual-cure or tri-cure polymerizable dental composition is provided with at least one functional chemical. The dental composition is divided into a three-part composition to avoid stability issues caused by degradation and/or loss of function of one component in the extended presence of another component, and the three parts are packaged in a tri-barrel syringe or cartridge delivery system to avoid premature chemical interaction between the functional chemical, redox initiator and/or acid/base.

26 Claims, No Drawings

DENTAL COMPOSITIONS HAVING SPECIAL FUNCTIONALITY AND A TRI-BARREL PACKAGING AND DELIVERY SYSTEM THEREFOR

CROSS REFERENCE TO RELATED APPLICATION

Pursuant to 37 C.F.R. §1.78(a)(4), this application claims the benefit of and priority to prior filed Provisional Application Nos. 61/410,171 filed Nov. 4, 2010 and 61/410,565 and 61/410,443 filed Nov. 5, 2010, which are expressly incorporated herein by reference.

FIELD OF THE INVENTION

The present invention is directed to dental compositions and, more particularly, to a multi-part composition and a packaging and delivery system for its use.

BACKGROUND OF THE INVENTION

Two-part dental compositions with self-cure mechanisms are currently being used as adhesives, cavity liners/bases, filling materials, endodontic sealers, or cements. The benefits for having a self-cure mechanism include unlimited depth of cure and the ability to cure in areas where there is limited or no light access. When the two parts are mixed together, the mixed composition will self-cure or harden on its own. The self-curing mechanism can be ionically through acid-base reaction, free-radically through a redox initiator system comprising a reducing agent and an oxidizing agent, or a combination of both. In addition to a self-curing mechanism, a photo-initiator can also be incorporated in the composition to make it also light-curable. The above three curing mechanisms can be used singularly or in combination so the two-part composition can be self-curable, dual-curable, or tri-curable. Examples of ionically curable compositions include zinc phosphate cement, zinc carboxylate cement, glass ionomer cement/liner/filling material/sealant, and resin-modified glass ionomer cement/liner/filling material/sealant. Examples of free-radically curable compositions incorporating a redox-initiator system include self-cure or dual-cure resin cement, composite filling material, core buildup materials, adhesive, cavity liner/base, endodontic sealer, and endodontic filling material. A photo-initiator can be included to make these compositions dual-curable (i.e. both self-curable and light-curable). Some systems such as resin-modified glass-ionomers can be tri-curable, i.e. having all-three curing mechanisms: ionically, free-radically through a redox initiator and free-radically through a photo-initiator.

It is often desirable to impart additional functionality to the above two-part dental compositions besides the basic function of restoring defective dentition. The additional functionality can be achieved by incorporating one or more functional chemicals or compounds. The list of functional chemicals/compounds includes a redox indicator, a pH indicator, a photobleachable dye, an acidic compound, a fluorescent compound, a fluoride releasing agent, an antimicrobial compound, or a combination of above. These functional chemicals/compounds impart a special property to the composition or aid the dentist in carrying out the restorative procedures.

However, stability issues can arise when these functional chemicals or compounds are incorporated into a two-part self-cure, dual-cure or tri-cure composition as at least one of the following issues may exist: (1) the functional chemical is not stable in the presence of the redox initiator (free-radically curing) or acid/base (ionically curing) of the two-part composition so that the functional chemical loses its intended function; (2) the redox initiator (free-radically curing) or acid/base (ionically curing) of the two-part composition is not stable in the presence of the functional chemical, causing shelf-life stability issues; and/or (3) the functional chemical interacts with the redox initiator (free-radically curing) or acid/base (ionically curing) of the two-part composition, forming an unacceptable coloration or color change during storage prior to use.

There is thus a need for a dental material that includes a special functionality without unintended instability of one component in the presence of another or premature reactions therebetween.

SUMMARY OF THE INVENTION

The present disclosure is directed to a three-part polymerizable dental composition. The composition includes (a) one or more polymerizable monomers each having at least one ethylenically unsaturated group, (b) one or more finely divided fillers, (c) a reducing agent, (d) an oxidizing agent, and (e) a functional chemical selected from the group consisting of a redox indicator, a pH indicator, a photobleachable dye, an acidic compound, a fluorescent compound, a fluoride releasing agent, and an antimicrobial compound, or any combination thereof. The reducing agent (c) and the oxidizing agent (d) form a redox initiator system, and a mixed composition is formed by mixing together three parts wherein a first part comprises (c), a second part comprises (d), a third part comprises (e), at least one of the first, second and third parts comprises (a), and at least one of the first, second and third parts comprises (b).

DETAILED DESCRIPTION OF THE INVENTION

The present invention is directed to resolving the above mentioned stability issue by dividing the self-cure, dual-cure or tri-cure composition incorporating at least one functional chemical into a three-part composition and packaging the three-part composition into a tri-barrel cartridge delivery system to avoid the chemical interaction between the functional chemical, redox initiator and/or acid/base.

In one embodiment, a three-part polymerizable dental composition is packaged inside three barrels of a tri-barrel cartridge assembly with each barrel containing one part of the three-part composition wherein the three-part polymerizable dental composition comprises:

(a) one or more polymerizable monomers each having at least one ethylenically unsaturated group,
(b) one or more finely divided fillers,
(c) a reducing agent,
(d) an oxidizing agent, and
(e) a functional chemical selected from the group consisting of a redox indicator, a pH indicator, a photobleachable dye, an acidic compound, a fluorescent compound, a fluoride releasing agent, an antimicrobial compound, or a combination thereof, wherein the reducing agent (c) and the oxidizing agent (d) form a redox initiator system that, when the components (a)-(e) of the composition are homogeneously mixed together, can initiate the polymerization of the polymerizable monomers (a) and cause the composition to harden.

As used herein, "a" means "one or more" such that, for example, "a polymerizable monomer" means "one or more polymerizable monomers" and "a" and "one or more" may be used interchangeably.

When the composition is homogenously mixed, the reducing agent (c) and oxidizing agent (d) of the redox initiator system come into contact with each other, at which time they will undergo a redox reaction, generate free radicals, initiate the polymerization of the polymerizable monomer (a), and cause the gellation and hardening (or curing) of the composition.

In one embodiment, the three-part polymerizable dental composition is packaged inside three barrels of a tri-barrel cartridge assembly with each barrel containing one part of the three-part composition. When two or more different types of functional chemicals (e.g. a redox indicator and an acidic compound) are incorporated in the 3-part composition, they can be incorporated into one composition in one barrel or different compositions in different barrels with the goal of achieving the best chemical stability for the 3-part composition.

Each barrel has an exit opening for dispensing the composition. Three plungers, either separate or connected to each other, are used to dispense the composition from each respective barrel. Rubber pistons either separated from or connected to the plungers can be used to provide a good seal. Alternatively, plungers with a rubber o-ring at or near the end can be used to provide a good seal. In one embodiment, the three barrels are molded together. In another embodiment, the three barrels are molded separately and the three barrels can be attached to a common fixture and the paste can be dispensed simultaneously. In another embodiment, the three barrels are molded separately and the three barrels can be placed inside a single holder for housing three barrels and the paste can be dispensed simultaneously. In another embodiment, the three barrels are molded separately and the three barrels can be placed inside three individual holders that are either molded together or attached to a common fixture, and the paste can be dispensed simultaneously. In another embodiment, the first two barrels are molded together and the third barrel can be attached to the assembly containing the first two barrels, and the paste can be dispensed simultaneously. In another embodiment, a fixture is molded together with the first barrel and the other two barrels can be attached to the fixture, and the paste can be dispensed simultaneously.

The pastes are dispensed by applying pressure to the plunger for each barrel. In one embodiment, the three-part composition is dispensed through the exit opening of each barrel of the tri-barrel cartridge assembly and manually mixed with a spatula to form a homogeneously mixed composition. In another embodiment, a static mixer containing at least one static mixing element is attached to the three exit openings of the tri-barrel cartridge assembly and a homogeneously mixed composition is obtained automatically when the composition is dispensed from the assembly.

The three-part composition, once dispensed from the barrels and mixed homogeneously, will polymerize and form a hardened composition through free-radical polymerization or the combination of free-radical polymerization and acid-base ionic reaction.

Any barrel cross-sectional area ratios can be used for the three barrels to control the volume ratio of the three parts. In one embodiment, the cross-sectional area ratio of three barrels is x:y:z wherein x, y, and z each can be 1 to 20 with "1" designating the barrel with the smallest cross-sectional area. For example, the cross-sectional area ratio of the three barrels can be 20:1:1, 20:1:15, 3:2:1, 1:5:5, 4:1:1; 2:2:1, or 1:1:1. In one embodiment, the cross-sectional area ratio of three barrels is x:y:z wherein x, y, and z each can be 1 to 10. In another embodiment, the cross-sectional area ratio of three barrels is x:y:z wherein x, y, and z each can be 1 to 5. While the examples provided recite integers for the values of x, y and z, the invention is not so limited, as any fractional value may also be used for any of x, y and z, for example, a ratio of 3.2:2.5:1.

For component (a), one or more polymerizable monomers each having at least one ethylenically unsaturated group can be incorporated into the composition. Examples of ethylenically unsaturated groups include, but are not limited to, acrylate, methacrylate, acrylamide, methacrylamide, and vinyl group. Examples of polymerizable monomers include, but are not limited to, the following: hydroxyethyl (meth)acrylate {(meth)acrylate=acrylate or methacrylate}, hydroxypropyl (meth)acrylate, hydroxybutyl (meth)acrylate, glycerol di(meth)acrylate, glycerol mono(meth)acrylate, methyl (meth)acrylate, ethyl (meth)acrylate, propyl (meth)acrylate, butyl (meth)acrylate, hexyl (meth)acrylate, octyl (meth)acrylate, lauryl (meth)acrylate, decyl (meth)acrylate, tridecyl (meth)acrylate, 2-ethoxyethyl (meth)acrylate, 2'-ethoxy-2-ethoxyethyl (meth)acrylate, ethyleneglycol di(meth)acrylate, diethyleneglycol di(meth)acrylate, triethyleneglycol di(meth)acrylate (TEGDMA), tetraethyleneglycol di(meth)acrylate, polyethyleneglycol mono-(meth)acrylate, polyethyleneglycol di-(meth)acrylate, polypropyleneglycol mono-(meth)acrylate, polypropyleneglycol di-(meth)acrylate, polytetramethyleneglycol mono-(meth)acrylate, polytetramethyleneglycol di-(meth)acrylate, hexanediol di(meth)acrylate, trimethyloylpropane tri(meth)acrylate, ethoxylated trimethyloylpropane tri(meth)acrylate, UDMA (reaction product of 2-hydroxyethyl methacrylate with 2,4,4-trimethylhexane diisocyanate), 2,2-bis [4-(2-hydroxy-3-methacryloylpropoxy)-phenyl]-propane (Bis-GMA), ethoxylated bisphenol A dimethacrylate ("EB-PADMA-n", n=total number of moles of ethylene oxide in the molecule, with 2-20 units being preferred), tetrahydrofurfuryl (meth)acrylate, N,N'-methylenebis(acrylamide), N,N'-ethylenebis(acrylamide), N,N'-butylenebis(acrylamide), or a mixture thereof. In one embodiment, component (a) comprises at least one polymerizable monomer having at least one hydroxyl group. Examples of hydroxyl-containing polymerizable monomers include, but are not limited to, hydroxyethyl (meth)acrylate, hydroxypropyl (meth)acrylate, hydroxybutyl (meth)acrylate, glycerol di(meth)acrylate, glycerol mono(meth)acrylate, 2,2-bis[4-(2-hydroxy-3-methacryloylpropoxy)-phenyl]-propane (Bis-GMA).

In one embodiment, component (a) comprises one or more polymerizable monomers having at least two ethylenically unsaturated groups.

The concentration of component (a) ranges from 1% (w/w) to 99% (w/w) of the composition. In one embodiment, the concentration of component (a) ranges from 10% (w/w) to 80% (w/w) of the composition. In one embodiment, the concentration of component (a) ranges from about 20% (w/w) to 70% (w/w) of the composition.

For component (b), one or more fillers can be incorporated into the composition. Examples of fillers include, but are not limited to, inorganic metal, salt, oxide, fluoride, nitride, silicate glass, aluminosilicate glass, aluminoborosilicate glass, fluoroaluminosilicate glass, quartz, colloidal silica, precipitated silica, zirconia-silica, mixed oxides fused together, polymeric filler, and/or polymerized composite fillers with inorganic particles. In one embodiment, inorganic fillers for increased x-ray contrast ability include metals, salts, oxides, fluorides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these. Examples include barium sulfate, silver, strontium fluoride, barium fluoride, ytterbium fluoride, yttrium fluoride, barium tungstate, zinc oxide, bismuth (III) oxide, bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate, etc. Fumed silica, colloidal silica, or precipitated silica can also be incorporated to improve the dispersion of the filler, as well as the rheological and handling properties of the composition. Examples of colloidal silicas are the Aerosil series such as OX-50, OX-130, and OX-200 silica sold by Degussa (Ridgefield Park, N.J.), and Cab-O-Sil M5 and Cab-O-Sil TS-530 silica sold by Cabot Corp (Tuscola, Ill.). The filler may also include nanoparticles such as those obtained through a sol-gel process. Examples include, but are not limited to those disclosed in U.S. Pat. Nos. 4,567,030 and 5,609,675, the disclosure of each expressly incorporated by reference herein in its entirety. Mixtures of different fillers can be used. For inorganic fillers, the surface of the filler may be treated or coated with a coupling agent, such as gamma-methacryloyloxypropyltrimethoxy-silane (MPTMS), that enhances the interfacial bonding between the filler and resin matrix and improves mechanical properties.

In one embodiment, the mean particle size of the filler is less than 50 microns. In another embodiment, the mean particle size of the filler is less than 10 microns. In another embodiment, the mean particle size of the filler is less than 5 microns. In another embodiment, the mean particle size of the filler is less than 2 microns. The concentration of component (b) ranges from 0.5% (w/w) to 90% (w/w) of the composition. In one embodiment, the concentration of component (b) is greater than 10% (w/w), for example, greater than 30% (w/w) or greater than 40% (w/w) of the composition. In one embodiment, the concentration of component (b) is less than 90% (w/w), for example, less than 80% (w/w) or less than 70% (w/w) of the composition.

For component (c), one or more reducing agents can be used as long as it can form a redox initiator system with component (d) that will be capable of initiating the polymerization and hardening of component (a). Examples of reducing agents include, but are not limited to, a tertiary amine, aromatic sulfinate salt, aliphatic sulfinate salt, thiourea, substituted thiourea, Fe(II) salt, Cu(I) salt, Co(II) salt, ascorbic acid, ascorbic acid derivatives and salts, barbituric acid, and barbituric acid derivatives and salts including thiobarbituric acid and it's derivatives and salts. In one embodiment, the reducing agent is an aromatic tertiary amine. Examples of aromatic tertiary amines include, but are not limited to, N,N-dihydroxyethyl p-toluidine, N,N-dimethyl p-toluidine, N,N-dimethylaminophenylethyl alcohol, and N,N-dimethylaminophenylacetic acid. In one embodiment, the reducing agent is an aromatic sulfinate salt. Examples of aromatic sulfinate salts include, but are not limited to, sodium benzenesulfinate, potassium benzenesulfinate, sodium toluenesulfinate, and potassium toluenesulfinate. In one embodiment, the reducing agent is a substituted thiourea. Substituted thioureas include, but are not limited to, 1-(2-pyridyl)-2-thiourea, 1-benzoyl-3-(2-pyridyl)-2-thiourea, 1-acetyl-3-(2-pyridyl)-2-thiourea, 1-phenyl-3-(2-pyridyl)-2-thiourea, 1-(2-pyridyl)-2-thiourea, 1,3-di-(2-pyridyl)-2-thiourea, 1,1-dimethyl-3-(2-pyridyl)-2-thiourea, 1,1,3-trimethyl-3-(2-pyridyl)-2-thiourea, and 1-(2-tetrahydrofufuryl)-3-(2-pyridyl)-2-thiourea, 1-acetyl-2-thiourea, 1-(2-tetrahydrofurfuryl)-2-thiourea, 1,1,3,3-tetramethyl-2-thiourea, 1,1,3-trimethyl-2-thiourea, 1,1,3,3-tetrapropyl-2-thiourea, 1,1,3-trimethyl-2-thiourea, 1-benzoyl-2-thiourea, and 1-benzoyl-3-methyl-2-thiourea. The concentration of component (c) ranges from 0.01% (w/w) to 10.0% (w/w) of the composition. In one embodiment, the concentration of component (c) ranges from 0.1% (w/w) to about 5.0% (w/w) of the composition.

For component (d), one or more oxidizing agents can be used as long as it can form a redox initiator system with component (c) that will be capable of initiating the polymerization and hardening of component (a). Examples of oxidizing agents include, but are not limited to, peroxide, hydroperoxide, persulfate salt, permanganate salt, Cu(II) salt such as Cu(II) acetylacetonate, Cu(II) benzoylacetonate, and Cu(II) cyclohexylbutyrate, Fe(III) salt such as $FeCl_3$, Fe(III) benzoyl acetonate, and Fe(III) cyclohexylbutyrate, and Co(III) salt. Examples of peroxides and hydroperoxides include, but are not limited to, di-t-butyl peroxide, dibenzoyl peroxide, hydrogen peroxide, t-butyl hydroperoxide, t-amyl hydroperoxide, p-diisopropylbenzene hydroperoxide, cumene hydroperoxide, pinane hydroperoxide, p-methane hydroperoxide, and 1,1,3,3-tetramethylbutyl hydroperoxide. The concentration of component (d) ranges from 0.01% (w/w) to 10.0% (w/w) of the composition. In one embodiment, the concentration of component (d) ranges from 0.1% (w/w) to about 5.0% (w/w) of the composition.

One or more of the following ingredients can also be incorporated into at least one part of the three-part composition: a photo-initiator, a solvent, a colorant, a shelf-life stabilizer, and/or a UV stabilizer.

In one embodiment, the composition further comprises a photoinitiator. The photoinitiator can be any compound that would generate free radicals upon exposure to a light source and cause the polymerization or hardening of the composition. The light source can be any dental curing light that emits light in the visible or ultraviolet range. Examples of photoinitiators include, but are not limited to, benzoin, benzoin ethers and esters, 2,2-diethoxy acetophenone, diketone compounds such as camphorquinone and 1-phenyl-1,2-propanedione, monoacylphosphine oxide, bisacylphosphine oxide as disclosed in U.S. Pat. No. 4,792,632, which is expressly incorporated by reference herein in its entirety, diaryliodonium salt, triarylsulfonium salt, and a mixture of photoinitiators.

Additionally, a coinitiator can be used together with a photoinitiator to enhance curing efficiency. Coinitiators include tertiary amine and sulfinate compounds. Examples of coinitiators include, but are not limited to, ethyl 4-(N,N-dimethylamino) benzoate, 4-(N,N-dimethylamino) benzoic acid, 4-(N,N-dimethylamino) benzonitrile, 4-(N,N-dimethylamino) benzaldehyde, 2-(ethylhexyl)-4-(N,N-dimethylamino) benzoate, N,N-dimethylaminoethyl methacrylate, N,N-dimethylaminophenethyl alcohol, sodium benzenesulfinate, and sodium toluenesulfinate.

In one embodiment, a photoinitiator system includes the combination of camphorquinone and a tertiary amine. Examples of tertiary amines include, but are not limited to, ethyl 4-(N,N-dimethylamino) benzoate, 4-(N,N-dimethylamino) benzoic acid, 4-(N,N-dimethylamino) benzonitrile, 4-(N,N-dimethylamino) benzaldehyde, 2-(ethylhexyl)-4-(N,N-dimethylamino) benzoate, N,N-dimethylaminoethyl methacrylate, N,N-dimethylaminophenethyl alcohol. In another embodiment, a photoinitiator system includes bisacylphosphine oxide or monoacylphosphine oxide or the combination of camphorquinone and bisacylphosphine oxide or monoacylphosphine oxide. In one embodiment, a photoinitiator may be present at a concentration of 0.01% (w/w) to about 10% (w/w) of the composition. In another embodiment, a photoinitiator may be present at a concentration of 0.05% (w/w) to about 5% (w/w) of the composition.

In one embodiment, the composition further comprises a solvent. Useful solvents include water, methanol, ethanol, isopropanol, acetone, methyl ethyl ketone, ethylene glycol, and glycerin. In one embodiment, the solvent is water.

In one embodiment, the composition further comprises a colorant, a shelf-life stabilizer and/or a UV stabilizer. The colorants are used to achieve desired shade for matching tooth color and can be inorganic pigments or organic dyes. The stabilizer is a polymerization inhibitor or retarder to improve the shelf stability of the restorative material. Most commonly used stabilizers include 2,6-di-(tert-butyl)-4-methylphenol ("BHT") and 4-methoxyphenol ("MEHQ"). The UV absorber is used to improve the color stability of the dental material upon exposure to UV light. An example of UV absorber is 2-hydroxy-4-methoxybenzophenone ("UV-9").

In one embodiment, the functional chemical (e) is a redox indicator. A redox indicator is used to indicate the extent of curing through color change during curing. One or more redox indicators can be used as long as the redox indicator(s) can exhibit definite (preferably noticeable) color change during the curing of the mixed composition initiated by the redox initiator system comprising component (c) and component (d). The redox indicator exhibits an initial first color upon mixing of the two parts of the redox initiator system and then changes to a second or final color that is noticeably different from the first color during the curing or polymerization of the composition through the redox initiator system. In one embodiment, the color change (ΔE) during the curing of the mixed composition is at least 5. In one embodiment, the color change (ΔE) during the curing of the mixed composition is at least 20. In one embodiment, the color change (ΔE) during the curing of the mixed composition is at least 25. In one embodiment, the color change (ΔE) during the curing of the mixed composition is at least 30. By way of example, a color change measurement may be conducted using a portable Spectrophotometer (Model SP60, X-Rite Inc.) in reflectance mode against a white background of an opacity card (Form 2A, Leneta Co.). The color is expressed as L*a*b* using the CIELAB scale where L* defines the lightness, a* denotes the red/green value, and b* the yellow/blue value. For color measurement, 1 mm thick specimens may be used. The overall color change may then be calculated using the following equation:

$$\Delta E = \{(L^*_1 - L^*_0)^2 + (a^*_1 - a^*_0)^2 + (b^*_1 - b^*_0)^2\}^{1/2}$$

where $L^*_0$, $a^*_0$, and $b^*_0$ are the initial color coordinates of initial color before color change, and $L^*_1$, $a^*_1$, and $b^*_1$ are the color coordinates after color change.

In an exemplary embodiment, the first color is quite a distinctive color that can be easily perceived so that if the dentist decides to clean the excess material immediately (i.e. before gellation), the dentist can easily identify where the excess material is. In another exemplary embodiment, the redox indicator exhibits its color change close to the gellation point of the mixed composition so that if the dentist decides to clean the excess material in its gelled state, the excess material can be easily and cleanly removed in relatively large pieces or in a single piece. In one embodiment, the redox indicator exhibits its color change within 90 seconds of the gellation point of the mixed composition. In another embodiment, the redox indicator exhibits its color change within 60 seconds of the gellation point of the mixed composition. In yet another embodiment, the redox indicator exhibits its color change within 30 seconds of the gellation point of the mixed composition. In yet another embodiment, the redox indicator exhibits its color change within 15 seconds of the gellation point of the mixed composition. In yet another embodiment, the redox indicator exhibits its color change within 5 seconds of the gellation point of the mixed composition. The gellation point is a point at which an infinite polymer network first appears. In an exemplary embodiment, the second color is a colorless color, a neutral color or a not easily noticeable color so that the dental material does not leave an undesirable color after the material is fully set, resulting in improved esthetics for the restoration or other dental structure.

Examples of redox indicators include, but are not limited to, 2,2'-bipyridine (Ru complex), nitrophenanthroline (Fe complex), 1,10-phenanthroline (Fe complex), N-phenylanthranilic acid, N-ethoxychrysoidine, 2,2'-bipyridine (Fe complex), 5,6-dimethylphenanthroline (Fe complex), o-dianisidine, sodium diphenylamine sulfonate, diphenylbenzidine, diphenylamine, viologen, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, and toluylene red. In one embodiment, the redox indicators are selected from the group consisting of N-phenylanthranilic acid, o-dianisidine, sodium diphenylamine sulfonate, diphenylbenzidine, diphenylamine, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, and toluylene red. In another embodiment, the redox indicators are selected from the group consisting of sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, and toluylene red. In yet another embodiment, the redox indicators are selected from the group consisting of sodium 2,6-dibromophenol-indophenol, sodium 2,6-dichlorophenol-indophenol, and sodium o-cresol indophenol.

In one embodiment, a three-part dental composition comprises: 1) a first part composition comprising a polymerizable monomer having at least one ethylenically unsaturated group, and a reducing agent; 2) a second part composition comprising a polymerizable monomer having at least one ethylenically unsaturated group, and an oxidizing agent; and 3) a third part composition comprising a polymerizable monomer having at least one ethylenically unsaturated group, and a redox indicator. At least one of the first, second and third part compositions further comprises at least one finely divided filler. In one embodiment, each of the first, second and third part compositions further comprises at least one finely divided filler. The above three-part composition can further comprise one or more components selected from the group consisting of a photo-initiator, a solvent, colorant, a stabilizer, a UV stabilizer, and a functional chemical other than the redox indicator. The three-part dental composition is packaged inside three barrels of a tri-barrel cartridge assembly with each barrel containing one part of the three-part composition.

A method of using the above 3-part dental restorative composition comprising a redox indicator as the functional chemical is also provided. In one embodiment, the method includes the steps of: 1) homogeneously mixing the first, second and third part compositions of the 3-part composition just prior to application; 2) applying the mixed composition to a tooth structure and/or a prosthetic device with the mixed composition exhibiting a first color that is noticeably different from the tooth structure and/or the prosthetic device; 3) removing any excess composition from the tooth structure and/or prosthetic device before the composition changes its color and while it can be easily differentiated from the tooth structure and the prosthetic device; and 4) finishing/polishing the restoration or other dental structure after the dental composition changes to its second color that is noticeably different from its first color (i.e., after the gellation and/or the hardening of the composition). The method may additionally include a step of covering the dental composition with an oxygen barrier after step 3) to provide a more thorough curing of the dental composition without an oxygen-inhibited layer on the surface. The oxygen barrier can be a try-in gel or a glycerine gel that can be easily removed after the curing of the dental composition. The method may additionally include a step of light-curing the dental composition prior to step 4) when a photo-initiator is incorporated into the dental composition. The prosthetic device includes an inlay, an onlay, a crown, a crown and bridge, or a post.

In another embodiment, the method includes the steps: 1) homogeneously mixing the first, second and third part compositions of the 3-part composition just prior to application; 2) applying the mixed composition to tooth structure and/or a prosthetic device with the mixed composition exhibiting a first color; 3) removing any excess composition from the tooth structure and/or prosthetic device when the dental composition changes its color to a second color that is noticeably different from the first color (indicating the gellation of the restorative composition); and 4) finishing/polishing the restoration or other dental structure. The method may additionally include a step of light-curing the dental composition prior to step 4) when a photo-initiator is incorporated into the dental composition.

In one embodiment, the functional chemical (e) is a pH indicator. A pH indicator can be incorporated to indicate the extent of curing through color change during curing as a result of an acid-base curing reaction (e.g., neutralization) as in the case of resin-modified glass-ionomer or self-adhering resin cement. The distinctive color prior to curing could also serve as a visual aid to facilitate identifying and removing excess material before the material gels. The color change can indicate the material either gelled or fully cured (or nearly fully cured) so that the dentist knows precisely when to clean the excess material or finish/polish the restoration. The pH indicator may exhibit an initial first color upon mixing of the two parts and then change to a second color that is noticeably different from the first color during the acid-base curing reaction. The pH indicator may be an acid sensitive color change indicator that registers an increase in pH, or a base sensitive color change agent that registers a decrease in pH, for example. In one embodiment, the color change ($\Delta E$) during the curing of the mixed composition is at least 5. In one embodiment, the color change ($\Delta E$) during the curing of the mixed composition is at least 20. In one embodiment, the color change ($\Delta E$) during the curing of the mixed composition is at least 25. In one embodiment, the color change ($\Delta E$) during the curing of the mixed composition is at least 30. The color change ($\Delta E$) may be measured as described above. In an exemplary embodiment, the first color is quite a distinctive color that can be easily perceived so that if the dentist decides to clean the excess material immediately (i.e., before gellation), the dentist can easily identify where the excess material is. In another exemplary embodiment, the pH indicator exhibits its color change close to the gellation point of the mixed composition so that if the dentist decides to clean the excess material in its gelled state, the excess material can be easily and cleanly removed in relatively large pieces or in a single piece. In one embodiment, the pH indicator exhibits its color change within 90 seconds of the gellation point of the mixed composition. In one embodiment, the pH indicator exhibits its color change within 60 seconds of the gellation point of the mixed composition. In an exemplary embodiment, the second color is a colorless color, a neutral color or a not easily noticeable color so that restorative material does not leave an undesirable color after the material is fully set, resulting in improved esthetics for the restoration or other dental structure.

In one embodiment, the functional chemical (e) is a photobleachable dye so that the composition has a distinctive color prior to light-curing, but the color bleaches out with the activation of light or photo-curing. This would aid the identification and easy removal of excess material prior to curing or hardening of the material. In one embodiment, the color change ($\Delta E$) after photo-activation of the mixed composition is at least 5. In one embodiment, the color change ($\Delta E$) after photo-activation of the mixed composition is at least 20. In one embodiment, the color change ($\Delta E$) after photo-activation of the mixed composition is at least 30. The color change ($\Delta E$) may be measured as described above.

In one embodiment, the functional chemical (e) is an acidic compound to impart self-etch and self-adhering property to the composition so that the dental restorative procedures can be significantly simplified as no separate etching, priming and bonding are needed. The acidic compound can be a homopolymer or copolymer of an $\alpha,\beta$-unsaturated carboxylic acid that will ionically react with fluoroaluminosilicate filler, causing the hardening of the composition. The acidic compound can be any acidic compound containing an acidic moiety. The acidic moiety can be any acidic functional group. Examples of acidic moieties include, but are not limited to, sulfonic acid, sulfinic acid, carboxylic acid, carboxylic acid anhydride, phosphonic acid or its derivative, phosphoric acid or its derivative, with a derivative being a salt or ester of the respective acid. In one embodiment, the acidic compound is an acidic polymer. Examples of acidic polymers include, but are not limited to, a homopolymer or copolymer of an $\alpha,\beta$-unsaturated carboxylic acid. Examples of a homopolymer or copolymer of an $\alpha,\beta$-unsaturated carboxylic acid include, but are not limited to poly(acrylic acid), poly(acrylic acid-maleic acid) copolymer, and poly(acrylic acid-maleic acid-itaconic acid) copolymer. In one embodiment, the acidic compound is an acidic polymerizable monomer having at least one ethylenically unsaturated group and at least one acidic moiety. In one embodiment, the acidic polymerizable monomer contains at least one acidic moiety selected from the group consisting of phosphonic acid or its derivative, and phosphoric acid or its derivative. Examples include, but are not limited to, phenyl methacryloxyethyl phosphate, glyceryldimethacrylate phosphate, dipentaerithritol pentaacrylate phosphate, methacryloyloxybutyl phosphate, methacryloyloxyhexyl phosphate, methacryloyloxydecyl phosphate, hydroxyethylmethacrylate phosphate, and bis(hydroxyethylmethacrylate) phosphate, and any combination thereof. In another embodiment, the acidic monomer contains at least one acidic moiety selected from the group consisting of carboxylic acid and carboxylic anhydride. Examples include, but are not limited to, maleic acid, itaconic acid, methacrylic acid, acrylic acid, a polymerizable homopolymer or copolymer of an α, β-unsaturated carboxylic acid such as (meth)acrylated poly(acrylic acid), (meth)acrylated poly(acrylic acid) copolymer such as (meth)acrylated poly(acrylic acid-maleic acid) copolymer or (meth)acrylated poly(acrylic acid-maleic acid-itaconic acid) copolymer, maleic anhydride, 4-methacryloxyethyltrimellitic anhydride, 4-methacryloxyethyltrimellitic acid, any addition product of mono- or di-anhydride compound with an hydroxyalkylmethacrylate compound such as the addition product of pyromellitic acid anhydride and 2-hydroxyethyl methacrylate, the addition product of pyromellitic acid anhydride and glycerol dimethacrylate, the addition product of 3,3',4,4'-benzophenonetetracarboxylic dianhydride and hydroxyethyl methacrylate, and the addition product of phthalic anhydride and hydroxyethyl methacrylate, the addition product of maleic anhydride and glycerol dimethacrylate, and any combination thereof. Any combination of acidic compounds can be used in the current composition. An example of a self-adhering composition includes self-adhering resin cement as disclosed in U.S. Pat. No. 7,166,651, and resin-modified glass ionomer as disclosed in U.S. Pat. No. 5,154,762, which are expressly incorporated by reference herein in their entirety. These self-adhering compositions, when used in the tri-barrel delivery system in accordance with embodiments of the invention, are expected to have improved stability and performance.

In one embodiment, a three-part self-adhering dental composition comprises: 1) a first part composition comprising a polymerizable monomer having at least one ethylenically unsaturated group, and a reducing agent; 2) a second part composition comprising a polymerizable monomer having at least one ethylenically unsaturated group, and an oxidizing agent; and 3) a third part composition comprising an acidic compound; and wherein at least one of the first, second and third part compositions further comprises at least one finely divided filler. In one embodiment, each of the first, second and third part compositions further comprises at least one finely divided filler. In one embodiment, the acidic compound in the third part composition is an acidic polymerizable monomer having at least one ethylenically unsaturated group and at least one acidic moiety. In another embodiment, at least one of the fillers in the first part composition and second part composition is a fluoroaluminosilicate filler, and the acidic compound in the third part composition is a homopolymer or copolymer of an α,β-unsaturated carboxylic acid or a polymerizable homopolymer or copolymer of an α,β-unsaturated carboxylic acid, that can ionically react with fluoroaluminosilicate filler. In one embodiment, the third part composition further comprises a polymerizable monomer without any acidic moiety. The above three-part composition can further comprise one or more components selected from the group consisting of a photo-initiator, a solvent, colorant, a stabilizer, a UV stabilizer, and a functional chemical other than the acidic compound. The three-part dental composition is packaged inside three barrels of a tri-barrel cartridge assembly with each barrel containing one part of the three-part composition.

In one embodiment, the functional chemical (e) is an antimicrobial agent to impart an antimicrobial property, thereby inhibiting the secondary caries around the restoration. Examples of antimicrobial additives include, but are not limited to, benzalkonium chloride, iodoform, eugenol, zinc oxide, triclosan, alkyl 4-hydroxybenzoate, silicate glass powder containing silver and/or zinc, and zeolite powder containing silver and/or zinc ion(s). Useful antibacterial zeolites and their preparation are disclosed in U.S. Pat. Nos. 4,911,899 and 4,775,585, each of which is expressly incorporated by reference herein in its entirety.

In one embodiment, the functional chemical (e) is a fluoride releasing agent that can release fluoride into saliva or water. Examples of fluoride compounds include, but are not limited to, sodium fluoride, strontium fluoride, sodium hexafluorosilicate, zinc hexafluorosilicate, ytterbium fluoride, a salt formed by an amine and HF, a complex formed by an amine and $BF_3$, and any combination thereof.

In one embodiment, the functional chemical (e) is a fluorescent agent to impart a special optical property for better esthetics or as an aid for identifying the material in case there is a need to remove it.

In one embodiment, at least one of the reducing agent (c), oxidizing agent (d), and functional chemical (e) is microencapsulated. Microencapsulation may be achieved by methods known to one skilled in the art, for example using water soluble or water insoluble encapsulants.

The three-part composition can be an adhesive, cavity liner/base, filling material, core buildup material, endodontic sealer, endodontic filling material, pit/fissure sealant, or cement. The self-cure, dual-cure or tri-cure dental composition comprising a functional chemical can be used as a dental restorative composition, an endodontic composition, or an orthodontic composition. The self-cure, dual-cure or tri-cure dental composition comprising a functional chemical can be used as a cement for adhering a prosthetic device to tooth structure, a filling material, a core buildup material, liner/base, a pit/fissure sealant, an endodontic sealing and/or filling material for sealing and/or filling of a root canal, an orthodontic adhesive and/or cement material for adhering an orthodontic appliance to tooth surfaces. The prosthetic device includes an inlay, an onlay, a crown, a crown and bridge, or a post. In one embodiment, the self-cure, dual-cure or tri-cure dental composition comprising a redox indicator is used as a cement or a core buildup material.

EXAMPLES

Abbreviations for materials used in all examples:
BHT: 2,6-di-(tert-butyl)-4-methylphenol
Bis-GMA: 2,2-bis[4-(2-hydroxy-3-methacryloyl-propoxy)-phenyl]-propane
CHPO: cumene hydroperoxide
CQ: camphoroquinone
EBPADMA: ethoxylated bisphenol A dimethacrylate with 3-4 moles of ethylene oxide
EDMAB: ethyl 4-(N,N-dimethylamino) benzoate
GDM: glyceryldimethacrylate
GDM-P: glyceryldimethacrylate phosphate or glyceryldimethacrylate dihydrogen phosphate
HEMA: hydroxyethyl methacrylate
MEHQ: 4-methoxyphenol
NaDCPIP: sodium 2,6-dichlorophenol-indophenol
ODMAB: 2-ethylhexyl 4-(N,N-dimethylamino) benzoate
PTU: 1-(2-pyridyl)-2-thiourea ST-BAS: bariumaluminoborosilicate filler, mean particle size of 1.6 μm, and surface treated with γ-methacryloyloxypropyltrimethoxysilane TEGDMA: triethylenglycol dimethacrylate TS-530: surface treated fumed silica or colloidal silica (from Cabot Corp.)

UDMA: reaction product of 2-hydroxyethyl methacrylate with 2,4,4-trimethylhexane diisocyanate $YbF_3$: ytterbium fluoride (aggregated 40 nm ytterbium fluoride, and mean particle size of aggregated particle of 0.7 μm)

All two-part and three-part compositions were formulated by first mixing together all the monomers and any ingredients soluble in the resin mixture to make a homogeneous liquid mixture, and then blending the fillers into the liquid mixture to make the paste.

Comparative Example 1

A two-part paste/paste self-cure composition was made with the redox indicator NaDCPIP incorporated in the base paste. The base paste was made by mixing the following ingredients into a homogeneous composition: 3.45% w/w Bis-GMA; 8.31% w/w TEGDMA; 11.46% w/w EBPADMA; 10.87% w/w UDMA; 0.41% w/w PTU; 0.01% w/w NaDCPIP; 3.00% w/w TS-530; 47.50% w/w ST-BAS; and 15.00% w/w $YbF_3$. The catalyst paste was made by mixing the following ingredients into a homogeneous composition: 3.45% w/w Bis-GMA; 8.21% w/w TEGDMA; 10.97% w/w EBPADMA; 10.65% w/w UDMA; 0.05% w/w BHT; 1.17% w/w CHPO; 3.00% w/w TS-530; 47.50% w/w ST-BAS; and 15.00% w/w $YbF_3$. When the freshly made base paste and catalyst paste were mixed at 1:1 volume ratio, the mixed material gelled after 5 minutes and hardened (or set) after 5 minutes 45 seconds. The total color change ($\Delta E$) from 2 minute after mixing to 6 minutes after mixing was 41.3. The color change prior to and after gellation was quite significant and easily noticeable. The color of the material changed from dark purple prior to gellation to colorless after gellation.

Both the base paste and catalyst paste were subjected to accelerated aging at 50° C. for 3 weeks. When the aged base paste and aged catalyst paste were mixed at 1:1 volume ratio, the mixed material gelled after 5 minutes and hardened (or set) after 5 minutes 45 seconds. The total color change ($\Delta E$) from 2 minute after mixing to 6 minutes after mixing was only 12.9, which was drastically reduced compared to the color change (41.3) when the fresh pastes were mixed. The color change prior to and after gellation was not easily noticeable because the initial color was a faint purple color for the aged material instead of the dark purple color of the fresh material.

Comparative Example 2

A two-part paste/paste self-cure composition identical to that in Comparative Example 1 was made except the redox indicator NaDCPIP was incorporated in the catalyst paste instead of in the base paste. The base paste was made by mixing the following ingredients into a homogeneous composition: 3.45% w/w Bis-GMA; 8.31% w/w TEGDMA; 11.46% w/w EBPADMA; 10.87% w/w UDMA; 0.41% w/w PTU; 3.00% w/w TS-530; 47.50% w/w ST-BAS; and 15.00% w/w $YbF_3$. The catalyst paste was made by mixing the following ingredients into a homogeneous composition: 3.45% w/w Bis-GMA; 8.21% w/w TEGDMA; 10.97% w/w EBPADMA; 10.65% w/w UDMA; 0.05% w/w BHT; 1.17% w/w CHPO; 0.01% w/w NaDCPIP; 3.00% w/w TS-530; 47.50% w/w ST-BAS; and 15.00% w/w $YbF_3$. When the freshly made base paste and catalyst paste were mixed at 1:1 volume ratio, the mixed material gelled after 5 minutes and hardened (or set) after 6 minutes. The total color change ($\Delta E$) from 2 minute after mixing to 6 minutes after mixing was 25.2. The color of the material changed from light purple color prior to gellation to colorless after gellation. The color change prior to and after gellation for the mixture of fresh pastes was much less than that observed when the redox indicator is incorporated in the base paste as in Comparative Example 1 because the initial purple color is not as intense as that in Comparative Example 1, due to a possible stability issue when the redox indicator is incorporated in the catalyst paste.

Both the base paste and catalyst paste were subjected to accelerated aging at 50° C. for 3 weeks. When the aged base paste and aged catalyst paste were mixed at 1:1 volume ratio, the mixed material gelled after 5 minutes 15 seconds and hardened (or set) after 6 minutes 15 seconds. The total color change ($\Delta E$) from 2 minute after mixing to 6 minutes after mixing was further reduced to 21.2, making the color change associated with the gellation/hardening less noticeable. The color of the mixed paste was a light purple color.

Example 1

The two part paste/paste compositions in Comparative Examples 1 and 2 were formulated into a three-part paste/paste/paste composition, separating the redox indicator from both the reducing agent and the oxidizing agent of the redox initiator system. The first paste (base paste) was made by mixing following ingredients into a homogeneous composition: 3.45% w/w Bis-GMA; 8.37% w/w TEGDMA; 11.23% w/w EBPADMA; 10.87% w/w UDMA; 0.59% w/w PTU; 3.00% w/w TS-530; 47.50% w/w ST-BAS; and 15.00% w/w $YbF_3$. The second paste (catalyst paste) was made by mixing following ingredients into a homogeneous composition: 3.45% w/w Bis-GMA; 8.36% w/w TEGDMA; 10.60% w/w EBPADMA; 10.30% w/w UDMA; 0.07% w/w BHT; 1.73% w/w CHPO; 3.00% w/w TS-530; 47.50% w/w ST-BAS; and 15.00% w/w $YbF_3$. The third paste (incorporating the redox indicator) was made by mixing following ingredients into a homogeneous composition: 3.45% w/w Bis-GMA; 8.28% w/w TEGDMA; 11.72% w/w EBPADMA; 11.04% w/w UDMA; 0.015% w/w NaDCPIP; 3.00% w/w TS-530; 47.50% w/w ST-BAS; and 15.00% w/w $YbF_3$. When the three pastes were mixed at 1:1:1 volume ratio (yielding the same mixed composition as in the Comparative Examples 1 and 2), the mixed material gelled after 5 minutes 30 seconds and hardened (or set) after 6 minutes. The total color change ($\Delta E$) from 2 minute after mixing to 6 minutes after mixing was 43.9, larger than the mixed composition in both Comparative Examples 1 and 2. The color change prior to and after gellation was quite significant and easily noticeable. The color of the material changed from dark purple prior to gellation to colorless after gellation.

All three pastes were then subjected to accelerated aging at 50° C. for 3 weeks. When the aged pastes were mixed at 1:1:1 volume ratio, the mixed material gelled after 5 minutes 15 seconds and hardened (or set) after 6 minutes 15 seconds. The total color change ($\Delta E$) from 2 minute after mixing to 6 minutes after mixing was 34.3, much larger than the mixed composition of aged pastes in both Comparative Examples 1 (12.9) and 2 (21.2). The color change prior to and after gellation was quite significant and easily noticeable. The color of the material changed from medium purple prior to gellation to colorless after gellation. Therefore, for the aged pastes, only the three-part paste/paste/paste composition still exhibited a noticeable color change during the gellation/hardening reaction when the aged pastes were homogeneously mixed, while the two-part paste/paste compositions in Comparative Examples 1 and 2 did not provide an easy to detect color transition for the mixed composition of the aged pastes.

Comparative Example 3

A two-part paste/paste self-adhesive composition was made with the acidic monomer GDM-P incorporated in the catalyst paste (the acidic GDM-P cannot be incorporated in the base paste as it can react with the reducing agent PTU in the base). The base paste was made by mixing the following ingredients into a homogeneous composition: 15.73% w/w Bis-GMA; 10.49% w/w GDM; 8.74% w/w HEMA; 0.17% w/w CQ; 0.35% w/w EDMAB; 0.01% w/w MEHQ; 0.50% w/w PTU; 3.00% w/w TS-530; and 61.0% w/w ST-BAS. The catalyst paste was made by mixing the following ingredients into a homogeneous composition: 5.16% w/w Bis-GMA; 10.32% w/w GDM; 5.16% w/w HEMA; 13.76% w/w GDM-P; 0.03% w/w BHT; 1.58% w/w CHPO; 3.00% w/w TS-530; and 61.0% w/w ST-BAS. When the freshly made base paste and catalyst paste were mixed at 1:1 volume ratio, the mixed material gelled after 2 minutes and 45 seconds and hardened (or set) after 4 minutes. After both the base paste and catalyst paste were subjected to accelerated aging at 50° C. for 1 week, the catalyst paste containing GDM-P polymerized, exhibiting poor stability.

Example 2

The same overall composition based on the two-part paste/paste composition in Comparative Example 3 was formulated into a three-part paste/paste/paste composition, separating the GDM-P acidic monomer from both the reducing agent and the oxidizing agent of the redox initiator system. The first paste (base paste) was made by mixing the following ingredients into a homogeneous composition: 16.04% w/w Bis-GMA; 10.70% w/w GDM; 7.13% w/w HEMA; 0.36% w/w CQ; 0.71% w/w EDMAB; 0.03% w/w MEHQ; 1.03% w/w PTU; 3.00% w/w TS-530; and 61.0% w/w ST-BAS. The second paste (catalyst paste) was made by mixing the following ingredients into a homogeneous composition: 15.53% w/w Bis-GMA; 10.35% w/w GDM; 6.90% w/w HEMA; 0.03% w/w BHT; 3.18% w/w CHPO; 3.00% w/w TS-530; and 61.0% w/w ST-BAS.3.45%. The third paste (incorporating the acidic monomer GDM-P) was made by mixing the following ingredients into a homogeneous composition: 5.14% w/w Bis-GMA; 10.28% w/w GDM; 6.85% w/w HEMA; 13.71% w/w GDM-P; 0.02% w/w BHT; 3.00% w/w TS-530; and 61.0% w/w ST-BAS. When the three pastes were mixed at 1:1:2 volume ratio (yielding the same overall mixed composition as in the comparative example 3), the mixed material gelled after 2 minutes 45 seconds and hardened (or set) after 4 minutes (same as the mixed composition from the fresh base paste and catalyst paste in Comparative Example 3). After 1 week accelerated aging at 50° C., all three pastes were stable. When the aged pastes were mixed at 1:1:2 volume ratio, the mixed material gelled after 2 minutes 30 seconds and hardened (or set) after 3 minutes 45 seconds, which is close to that obtained for the mixed composition from fresh pastes. Therefore, when the acidic monomer GDM-P was separated from the oxidizing agent and reducing agent, a stable 3-part composition was obtained.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A three-part polymerizable dental composition in a tri-barrel cartridge assembly, comprising:
 first, second and third parts of the three-part polymerizable dental composition comprising:
  (a) one or more polymerizable monomers each having at least one ethylenically unsaturated group,
  (b) one or more finely divided fillers,
  (c) a reducing agent,
  (d) an oxidizing agent, and
  (e) a functional chemical selected from the group consisting of a redox indicator, and an acidic compound, or a combination thereof, wherein the acidic compound is an acidic polymerizable monomer having at least one ethylenically unsaturated group and at least one acidic moiety selected from the group consisting of phosphonic acid or its derivative, and phosphoric acid or its derivative,
 wherein the reducing agent (c) and the oxidizing agent (d) form a redox initiator system, and the first part comprises (c), the second part comprises (d), the third part comprises (e), at least one of the first, second and third parts comprises (a), and at least one of the first, second and third parts comprises (b); and
 the tri-barrel cartridge assembly comprising:
  first, second and third barrels separate from each other and separately containing the first, second and third parts, respectively, of the three-part polymerizable dental composition,
  a static mixer fluidicly coupled to an exit opening in each of the first, second and third barrels, the static mixer having a mixing element for forming a homogeneous mixture of the first, second and third parts prior to use, and
  a dispensing means for dispensing the homogeneous mixture from the static mixer of the tri-barrel cartridge assembly.

2. The composition of claim 1 wherein the reducing agent (c) is selected from the group consisting of a tertiary amine, an aromatic sulfinate salt, an aliphatic sulfinate salt, a thiourea, a substituted thiourea, a Fe(II) salt, a Cu(I) salt, a Co(II) salt, ascorbic acid, ascorbic acid derivatives and salts, barbituric acid, barbituric acid derivatives and salts, and any combination thereof.

3. The composition of claim 1 wherein the oxidizing agent (d) is selected from the group consisting of a peroxide, a hydroperoxide, a persulfate salt, a permanganate salt, a Cu(II) salt, a Fe(III) salt, a Co(III) salt, and any combination thereof.

4. The composition of claim 1 wherein the functional chemical (e) comprises the redox indicator, and wherein the mixed composition exhibits a first color upon mixing of the three parts and then undergoes a color change (ΔE) to a second color that is noticeably different from the first color during curing of the mixed composition through the redox initiator system, wherein the color change (ΔE) for a 1 mm thick specimen during the curing of the mixed composition is at least 5.

5. The composition of claim 4 wherein the redox indicator is selected from the group consisting of 2,2'-bipyridine (Ru complex), nitrophenanthroline (Fe complex), 1,10-phenanthroline (Fe complex), N-phenylanthranilic acid, N-ethoxychrysoidine, 2,2'-bipyridine (Fe complex), 5,6-dimethylphenanthroline (Fe complex), o-dianisidine, sodium diphenylamine sulfonate, diphenylbenzidine, diphenylamine, viologen, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, toluylene red, and any combination thereof.

6. The composition of claim 4 wherein the first color is distinctively different from that of a tooth structure to which the mixed composition is to be applied, and wherein the second color is a colorless color or a color similar to the tooth structure.

7. The composition of claim 1 wherein the functional chemical (e) further comprises a pH indicator, and wherein the mixed composition exhibits a first color upon mixing of the three parts and then undergoes a color change (ΔE) to a second color that is noticeably different from the first color through the acid-base neutralization reaction, wherein the color change (ΔE) for a 1 mm thick specimen is at least 5.

8. The composition of claim 1 wherein the functional chemical (e) further comprises a photobleachable dye, the three-part polymerizable dental composition further comprises a photo-initiator, the mixed composition has a color that is distinctively different from that of a tooth structure to which the mixed composition is to be applied prior to the activation of photo-curing, and the color bleaches out or changes to a distinctively different color with the activation of photo-curing.

9. The composition of claim 1 wherein the functional chemical (e) comprises the acidic compound, and wherein the at least one acidic moiety is selected from the group consisting of phenyl methacryloxyethyl phosphate, glyceryldimethacrylate phosphate, dipentaerithritol pentaacrylate phosphate, methacryloyloxybutyl phosphate, methacryloyloxyhexyl phosphate, methacryloyloxydecyl phosphate, hydroxyethylmethacrylate phosphate, and bis(hydroxyethylmethacrylate) phosphate, and any combination thereof.

10. The composition of claim 1 wherein the one or more finely divided fillers (b) include a fluoroaluminosilicate filler and the functional chemical (e) includes an acidic compound that is a homopolymer or copolymer of an α, β-unsaturated carboxylic acid and that will ionically react with the fluoroaluminosilicate filler.

11. The composition of claim 1 wherein each of the first, second and third parts includes one of the one or more finely divided fillers (e).

12. The composition of claim 1 wherein the functional chemical (e) further comprises an antimicrobial compound and wherein the antimicrobial compound is selected from the group consisting of benzalkonium chloride, iodoform, eugenol, zinc oxide, triclosan, alkyl 4-hydroxybenzoate, silicate glass powder containing silver, silicate glass powder containing zinc, silicate glass powder containing silver and zinc, zeolite powder containing silver ions, zeolite powder containing zinc ions, and zeolite powder containing silver and zinc ion, or any combination thereof.

13. The composition of claim 1 wherein the cross-sectional area ratio of the three barrels is x:y:z and x, y, and z are each 1.0 to 20.0.

14. A method of using a color-changing polymerizable dental composition, in which the composition comprises:
(a) one or more polymerizable monomers each having at least one ethylenically unsaturated group,
(b) one or more finely divided fillers,
(c) a reducing agent,
(d) an oxidizing agent, and
(e) a redox indicator,
wherein the composition is a three-part system with the first part comprising one of the one or more polymerizable monomers (a) and the reducing agent (c), the second part comprising one of the one or more polymerizable monomers (a) and the oxidizing agent (d), and the third part comprising the redox indicator (e), and wherein at least one of the one or more finely divided fillers (b) is incorporated in each of the first, second and third parts, and wherein the reducing agent (c) and the oxidizing agent (d) form a redox initiator system, the method comprising the steps of:
1) homogeneously mixing the first, second and third parts just prior to application to form a mixed composition, wherein the mixing initiates polymerization by the redox initiator system;
2) applying the mixed composition to a tooth structure and/or a prosthetic device with the mixed composition exhibiting a first color that is noticeably different from the tooth structure and/or prosthetic device, wherein the mixed composition exhibits a color change from the first color to a second color that is noticeably different from the first color during the polymerization;
3) removing any excess of the mixed composition from the tooth structure and/or prosthetic device before the mixed composition changes to the second color to form a structure; and
4) finishing/polishing the structure after the mixed composition changes to the second color, wherein the prosthetic device is selected from the group consisting of an inlay, an onlay, a crown, a crown and bridge, and a post.

15. The method of claim 14 wherein the three parts are packaged separately inside three barrels of three syringes prior to (1), with the first barrel containing the first part, the second barrel containing the second part, and the third barrel containing the third part.

16. The method of claim 14 wherein the three parts are packaged separately inside three barrels of a tri-barrel cartridge assembly prior to (1), with the first barrel containing the first part, the second barrel containing the second part, and the third barrel containing the third part, wherein each barrel in the tri-barrel cartridge assembly has an opening and a static mixer is attached to the openings and (1) is performed by dispensing the first, second and third parts from the barrels through the openings and into the mixer and homogeneously mixing in the mixer to form the mixed composition, and (2) is performed in part by dispensing the mixed composition from an exit opening of the mixer.

17. The method of claim 14 wherein the third part further comprises one of the one or more polymerizable monomers (a).

18. The method of claim 14 further comprising in the third part an acidic compound selected from the group consisting of an acidic polymer and an acidic polymerizable monomer having at least one ethylenically unsaturated group and at least one acidic moiety.

19. The method of claim 18 wherein the at least one acidic moiety is selected from the group consisting of phenyl methacryloxyethyl phosphate, glyceryldimethacrylate phosphate, dipentaerithritol pentaacrylate phosphate, methacryloyloxybutyl phosphate, methacryloyloxyhexyl phosphate, methacryloyloxydecyl phosphate, hydroxyethylmethacrylate phosphate, and bis(hydroxyethylmethacrylate) phosphate, and any combination thereof.

20. A method of using a color-changing polymerizable dental composition, in which the composition comprises:
 (a) one or more polymerizable monomers each having at least one ethylenically unsaturated group,
 (b) one or more finely divided fillers,
 (c) a reducing agent,
 (d) an oxidizing agent, and
 (e) a redox indicator,
 wherein the composition is a three-part system with the first part comprising one of the one or more polymerizable monomers (a) and the reducing agent (c), the second part comprising one of the one or more polymerizable monomers (a) and the oxidizing agent (d), and the third part comprising the redox indicator (e), and wherein at least one of the one or more finely divided fillers (b) is incorporated in each of the first, second and third parts, and wherein the reducing agent (c) and the oxidizing agent (d) form a redox initiator system, the method comprising the steps of:
 1) homogeneously mixing the first, second and third parts just prior to application to form a mixed composition, wherein the mixing initiates polymerization by the redox initiator system;
 2) applying the mixed composition to a tooth structure and/or a prosthetic device with the mixed composition exhibiting a first color, wherein the mixed composition exhibits a color change from the first color to a second color that is noticeably different from the first color during the polymerization;
 3) removing any excess composition from the tooth structure and/or prosthetic device when the mixed composition changes color to the second color that is noticeably different from the first color and that indicates the gellation of the mixed composition to form a structure; and
 4) finishing/polishing the structure, wherein the prosthetic device is selected from the group consisting of an inlay, an onlay, a crown, a crown and bridge, and a post.

21. The method of claim 20 wherein the three parts are packaged separately inside three barrels of three syringes prior to (1), with the first barrel containing the first part, the second barrel containing the second part, and the third barrel containing the third part.

22. The method of claim 20 wherein the three parts are packaged separately inside three barrels of a tri-barrel cartridge assembly prior to (1), with the first barrel containing the first part, the second barrel containing the second part, and the third barrel containing the third part, wherein each barrel in the tri-barrel cartridge assembly has an opening and a static mixer is attached to the openings and (1) is performed by dispensing the first, second and third parts from the barrels through the openings and into the mixer and homogeneously mixing in the mixer to form the mixed composition, and (2) is performed in part by dispensing the mixed composition from an exit opening of the mixer.

23. The method of claim 20 wherein the third part further comprises one of the one or more polymerizable monomers (a).

24. The method of claim 20 further comprising in the third part an acidic compound selected from the group consisting of an acidic polymer and an acidic polymerizable monomer having at least one ethylenically unsaturated group and at least one acidic moiety, wherein the at least one acidic moiety is selected from the group consisting of phenyl methacryloxyethyl phosphate, glyceryldimethacrylate phosphate, dipentaerithritol pentaacrylate phosphate, methacryloyloxybutyl phosphate, methacryloyloxyhexyl phosphate, methacryloyloxydecyl phosphate, hydroxyethylmethacrylate phosphate, and bis(hydroxyethylmethacrylate) phosphate, and any combination thereof.

25. A three-part polymerizable dental composition comprising:
 (a) one or more polymerizable monomers each having at least one ethylenically unsaturated group,
 (b) one or more finely divided fillers,
 (c) a reducing agent,
 (d) an oxidizing agent, and
 (e) a functional chemical selected from the group consisting of a redox indicator and an acidic compound, or a combination thereof, wherein the acidic compound is an acidic polymerizable monomer having at least one ethylenically unsaturated group and at least one acidic moiety selected from the group consisting of phosphonic acid or its derivative, and phosphoric acid or its derivative,
 wherein the reducing agent (c) and the oxidizing agent (d) form a redox initiator system, and
 wherein a first part comprises (c) but not (d) or (e), a second part comprises (d) but not (c) or (e), a third part comprises (e) but not (c) or (d), at least one of the first, second and third parts comprises (a), and at least one of the first, second and third parts comprises (b), and wherein a homogenous composition is formed by homogenously mixing together the first, second and third parts.

26. The composition of claim 25 wherein the functional chemical (e) comprises the redox indicator, and wherein the homogenous composition exhibits a first color upon homogenous mixing of the first, second and third parts and then undergoes a color change ($\Delta E$) to a second color that is noticeably different from the first color during curing of the homogenous composition through the redox initiator system, wherein the color change ($\Delta E$) for a 1 mm thick specimen during the curing of the homogenous composition is at least 5.

* * * * *

UNITED STATES PATENT AND TRADEMARK OFFICE
CERTIFICATE OF CORRECTION

| | | |
|---|---|---|
| PATENT NO. | : 9,522,099 B2 | Page 1 of 1 |
| APPLICATION NO. | : 13/288347 | |
| DATED | : December 20, 2016 | |
| INVENTOR(S) | : Xuejun Qian et al. | |

It is certified that error appears in the above-identified patent and that said Letters Patent is hereby corrected as shown below:

In the Specification

In Column 13, Line 46, "from 2 minute" should read --from 2 minutes--.

In Column 14, Line 6, "from 2 minute" should read --from 2 minutes--.

In Column 14, Line 21, "from 2 minute" should read --from 2 minutes--.

In Column 14, Line 52, "from 2 minute" should read --from 2 minutes--.

In Column 14, Line 63, "from 2 minute" should read --from 2 minutes--.

In Column 15, Line 51, "w/w ST-BAS.3.45%." should read --w/w ST-BAS.--.

In the Claims

In Column 18, Line 2, Claim 12, "and zinc ion," should read --and zinc ions,--.

Signed and Sealed this
Second Day of May, 2017

Michelle K. Lee
*Director of the United States Patent and Trademark Office*